United States Patent
Kuhara et al.

(10) Patent No.: US 9,927,502 B2
(45) Date of Patent: Mar. 27, 2018

(54) RESPIRATION SUPPRESSING MAT AND MAGNETIC RESONANCE IMAGING APPARATUS AND METHOD

(75) Inventors: Shigehide Kuhara, Otawara (JP); Ayako Ninomiya, Tokyo (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 1575 days.

(21) Appl. No.: 12/032,251

(22) Filed: Feb. 15, 2008

(65) Prior Publication Data

US 2008/0200800 A1    Aug. 21, 2008

(30) Foreign Application Priority Data

Feb. 19, 2007    (JP) .................................. 2007-038663

(51) Int. Cl.
| | |
|---|---|
| A61B 5/055 | (2006.01) |
| G01R 33/28 | (2006.01) |
| A61B 90/14 | (2016.01) |
| A61B 90/00 | (2016.01) |

(52) U.S. Cl.
CPC ............ *G01R 33/28* (2013.01); *A61B 90/14* (2016.02); *A61B 2090/374* (2016.02)

(58) Field of Classification Search
CPC .............................. A61B 5/1135; A61B 5/113
USPC .......................... 450/4, 85, 94–156; 600/534
See application file for complete search history.

(56) References Cited

U.S. PATENT DOCUMENTS

| | | | |
|---|---|---|---|
| 4,719,424 A * | 1/1988 | Jimbo et al. .................. 324/309 |
| 4,930,508 A * | 6/1990 | Shimoni et al. .............. 600/410 |
| 4,960,118 A * | 10/1990 | Pennock ................... 128/200.24 |
| 4,989,612 A * | 2/1991 | Fore .............................. 600/534 |
| 5,035,244 A * | 7/1991 | Stokar ........................... 600/410 |
| 5,088,501 A * | 2/1992 | Niewisch ...................... 600/534 |
| 5,107,846 A * | 4/1992 | Atlas ............................. 600/479 |
| 5,251,629 A | 10/1993 | Koizumi et al. |
| 5,853,005 A * | 12/1998 | Scanlon ........................ 600/459 |
| 6,292,684 B1 * | 9/2001 | Du ..................... G01R 33/5676 324/309 |
| 6,447,443 B1 * | 9/2002 | Keogh et al. .................... 600/37 |
| 6,816,266 B2 * | 11/2004 | Varshneya et al. ........... 356/477 |
| 6,875,176 B2 * | 4/2005 | Mourad et al. ............... 600/442 |
| 6,980,679 B2 * | 12/2005 | Jeung et al. .................. 382/128 |
| 6,984,207 B1 * | 1/2006 | Sullivan et al. .............. 600/301 |
| 7,154,991 B2 * | 12/2006 | Earnst et al. .................... 378/65 |
| 7,175,644 B2 * | 2/2007 | Cooper et al. ................ 606/191 |
| 2002/0095139 A1 * | 7/2002 | Keogh et al. ..................... 606/1 |
| 2002/0183611 A1 * | 12/2002 | Fishbein et al. ............. 600/410 |
| 2003/0095263 A1 * | 5/2003 | Varshneya et al. ........... 356/477 |

(Continued)

FOREIGN PATENT DOCUMENTS

| | | |
|---|---|---|
| JP | 2-104011 | 8/1990 |
| JP | 4-22907 | 2/1992 |

(Continued)

*Primary Examiner* — Serkan Akar
*Assistant Examiner* — Farshad Negarestan
(74) *Attorney, Agent, or Firm* — Oblon, McClelland, Maier & Neustadt, L.L.P.

(57) ABSTRACT

A respiration suppressing member includes a main body of an elastic material which is formed into a shape having a pressurizing portion for pressurizing that portion of the abdomen of a subject under imaging diagnosis by a medical modality which is located below the sternum and between the right and left ribs of the subject.

10 Claims, 10 Drawing Sheets

(56) References Cited

U.S. PATENT DOCUMENTS

| | | | |
|---|---|---|---|
| 2003/0188757 A1* | 10/2003 | Yanof et al. | 128/916 |
| 2004/0147832 A1* | 7/2004 | Fishbein et al. | 600/410 |
| 2004/0210214 A1* | 10/2004 | Knowlton | 606/41 |
| 2004/0254773 A1* | 12/2004 | Zhang et al. | 703/11 |
| 2005/0085801 A1* | 4/2005 | Cooper et al. | 606/14 |
| 2005/0119560 A1* | 6/2005 | Mostafavi | A61B 5/1135 600/425 |
| 2005/0187071 A1* | 8/2005 | Yamashita et al. | 482/1 |
| 2006/0004281 A1* | 1/2006 | Saracen | 600/414 |
| 2006/0063982 A1* | 3/2006 | Sullivan et al. | 600/301 |
| 2006/0183999 A1* | 8/2006 | Lorenz et al. | 600/410 |
| 2006/0229594 A1* | 10/2006 | Francischelli et al. | 606/27 |
| 2006/0229641 A1* | 10/2006 | Gupta et al. | 606/130 |
| 2006/0244445 A1* | 11/2006 | Sussman et al. | 324/307 |
| 2006/0245543 A1* | 11/2006 | Earnst et al. | 378/65 |
| 2007/0016005 A1* | 1/2007 | Timinger et al. | 600/424 |
| 2007/0039101 A1* | 2/2007 | Luginbuhl et al. | 5/600 |

FOREIGN PATENT DOCUMENTS

| | | |
|---|---|---|
| JP | 2000-41970 | 2/2000 |
| JP | 2000-157507 | 6/2000 |
| JP | 2004-57226 | 2/2004 |

* cited by examiner

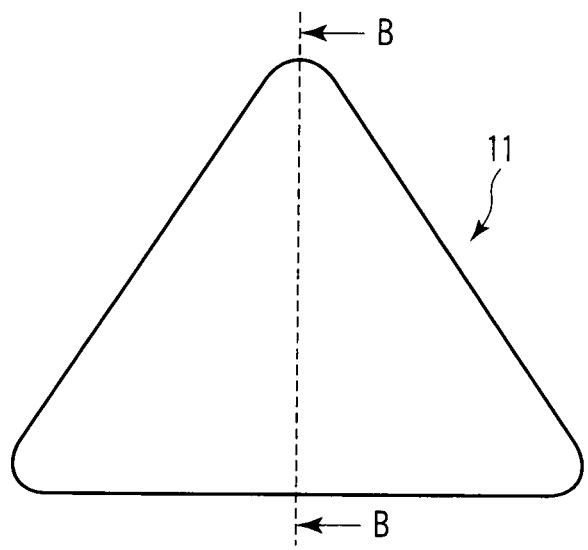 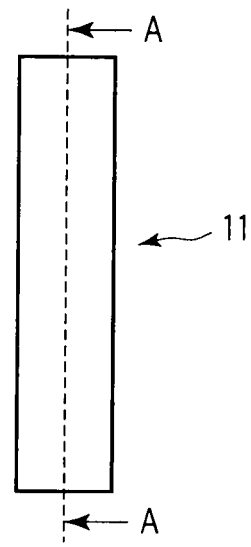
FIG. 2A  FIG. 2B
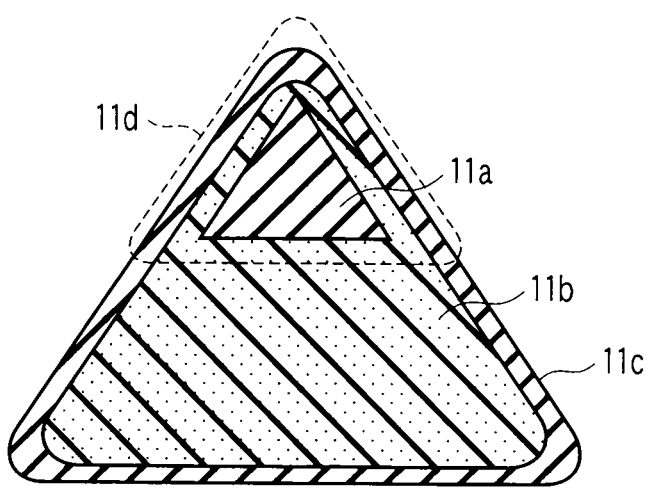 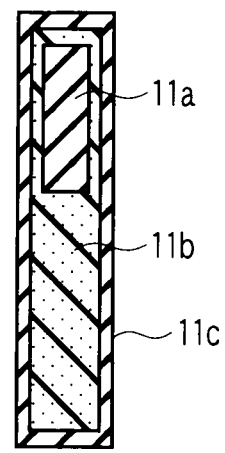
FIG. 2C  FIG. 2D

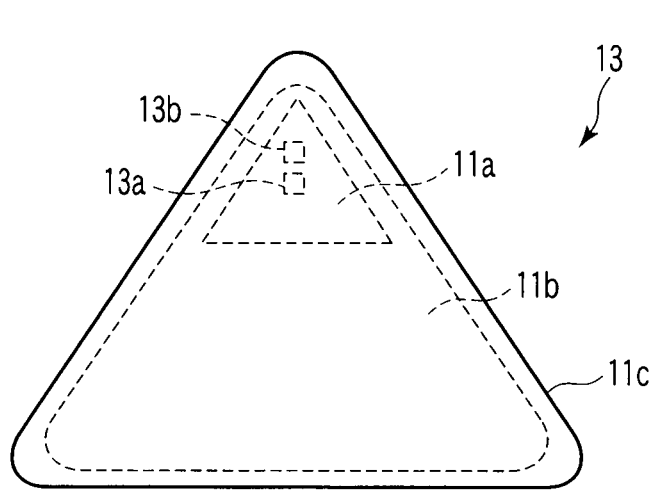
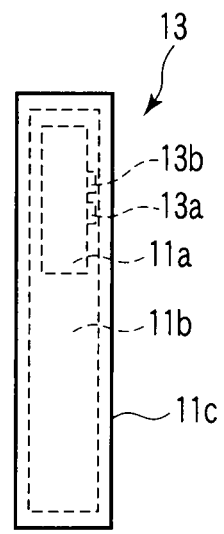
FIG. 4A  FIG. 4B
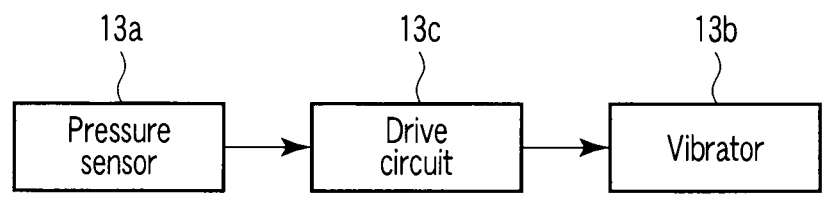
FIG. 5

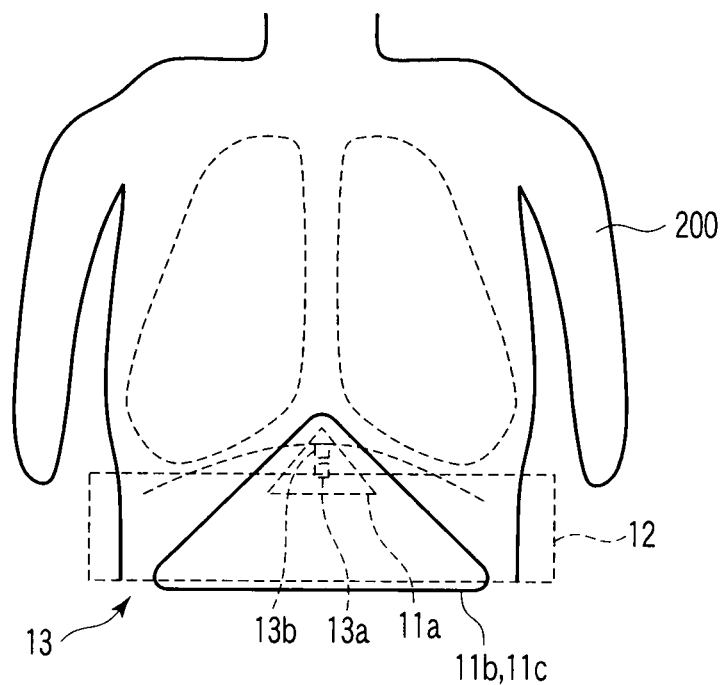
F I G. 6A
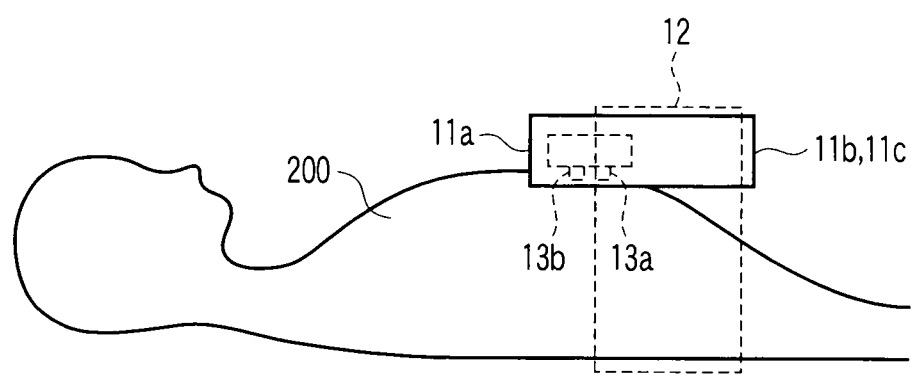
F I G. 6B

RESPIRATION SUPPRESSING MAT AND MAGNETIC RESONANCE IMAGING APPARATUS AND METHOD

CROSS-REFERENCE TO RELATED APPLICATIONS

This application is based upon and claims the benefit of priority from prior Japanese Patent Application No. 2007-038663, filed Feb. 19, 2007, the entire contents of which are incorporated herein by reference.

BACKGROUND OF THE INVENTION

1. Field of the Invention

The present invention relates to a respiration suppressing member which is attached to the body of a subject in order to suppress the respiration-based motion of his or her internal organs and a magnetic resonance imaging apparatus and method using such a respiration suppressing member.

2. Description of the Related Art

In order to produce an image of the coronary artery of a human body (subject) under examination by means of magnetic resonance imaging, an imaging technique is used which, using a three-dimensional steady state free precession (3D SSFP) sequence, produces images of the subject while he or she is intercepting breathing or respiring naturally. In particular, with the whole heart MR coronary angiography (WH MRCA) which visualizes the coronary artery in the whole heart, breathing intercept can provide insufficient spatial resolution. To avoid this problem, a technique is used which, under natural respiration, monitors the respiration-based motion by detecting the location of the diaphragm on the basis of nuclear magnetic resonance (NMR) signals and changes the imaging position to fit the detected respiration-based motion. Further, a technique is used which sets a constant threshold on the range of respiration-based motion and ceases the collection of NMR signals when the motion exceeds that threshold. That is, for example, data collection is made only when the peak of signals resulting from one-dimensional Fourier transform of NMR signals collected from such a region R as shown in FIG. 12A falls in the allowable range between upper and low limiting thresholds USL and LSL as shown in FIG. 12B. In addition, imaging is performed while the imaging position is changed to fit the respiration-based motion.

By so doing, 3D images of considerably high resolution can be obtained even under natural respiration.

The related techniques are known from, for example, JP-A Nos. 2000-041970, 2000-157507, and 2004-057226.

However, when the respiration level is not constant but gradually falls or rises, the portion corresponding to the location of the diaphragm in the signals resulting from one-dimensional Fourier transform of NMR signals will deviate from the allowable range as shown in FIG. 12C. In such a case, the imaging time might be increased. In the worst case, examination could not be completed.

For this reason, as shown in FIG. 13, a belt-like fixing means 500 is used to fix the subject's abdomen. In this case, although the motion of the diaphragm is suppressed, the thorax will also be subjected to pressure. Thus, the subject might breathe with difficulty. Conversely, trying to avoid such a situation results in the effect of suppressing the motion of the diaphragm being lessened.

BRIEF SUMMARY OF THE INVENTION

From such circumstances, it is desired to efficiently suppress the motion of the diaphragm without greatly pressurizing the thorax.

According to a aspect of the present invention, there is provided a respiration suppressing member comprising a main body of an elastic material which is formed into a shape having a pressurizing portion for pressurizing that portion of the abdomen of a subject under imaging diagnosis by a medical modality which is located below the sternum and between the right and left ribs of the subject.

According to another aspect of the present invention, there is provided a magnetic resonance imaging apparatus comprising: a static field magnet which generates a static magnetic field; an application unit which applies a radio-frequency magnetic field and gradient magnetic fields to a subject placed in the static magnetic field in accordance with a pulse sequence; a respiration suppressing member which has a main body of an elastic material formed into a shape having a pressurizing portion and is attached to the subject in a state in which pressurizes that portion of the abdomen of the subject which is located below the sternum and between the right and left ribs of the subject; a receiver which receives magnetic resonance signals emitted from the subject subjected to the radio-frequency magnetic field and the gradient magnetic fields; and a reconstruction unit which reconstructs an image associated with the subject on the basis of the magnetic resonance signals received by the receiver.

According to another aspect of the present invention, there is provided a magnetic resonance imaging method comprising the steps of: obtaining a signal representative of the respiration-based motion of a subject in a state in which pressure is applied to that portion of the abdomen of the subject which is located below the sternum and between the right and left ribs of the subject; collecting magnetic resonance signals by means of imaging scan of a desired region of the subject while changing the imaging position in synchronism with the signal representative of the respiration-based motion in that state; and reconstructing an image of the desired region of the subject on the basis of the collected magnetic resonance signals.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a plan view of the respiration suppressing member shown in FIG. 1;

FIG. 2B is a side view of the respiration suppressing member of FIG. 1;

FIG. 2C is a sectional view taken along line A-A of FIG. 2B;

FIG. 2D is a sectional view taken along line B-B of FIG. 2A;

FIG. 4A is a plan view of a respiration suppressing member according to a second embodiment;

FIG. 4B is a side view of the respiration suppressing member shown in FIG. 4A;

FIG. 5 shows an electrical arrangement of the respiration suppressing member of the second embodiment;

FIGS. 6A and 6B are diagrams showing the state in which the respiration suppressing member shown in FIGS. 4A and 4B is attached to the abdomen of a subject;

DETAILED DESCRIPTION OF THE INVENTION

The embodiments of the present invention will be described hereinafter with reference to the accompanying drawings.

First Embodiment

Figure 1:
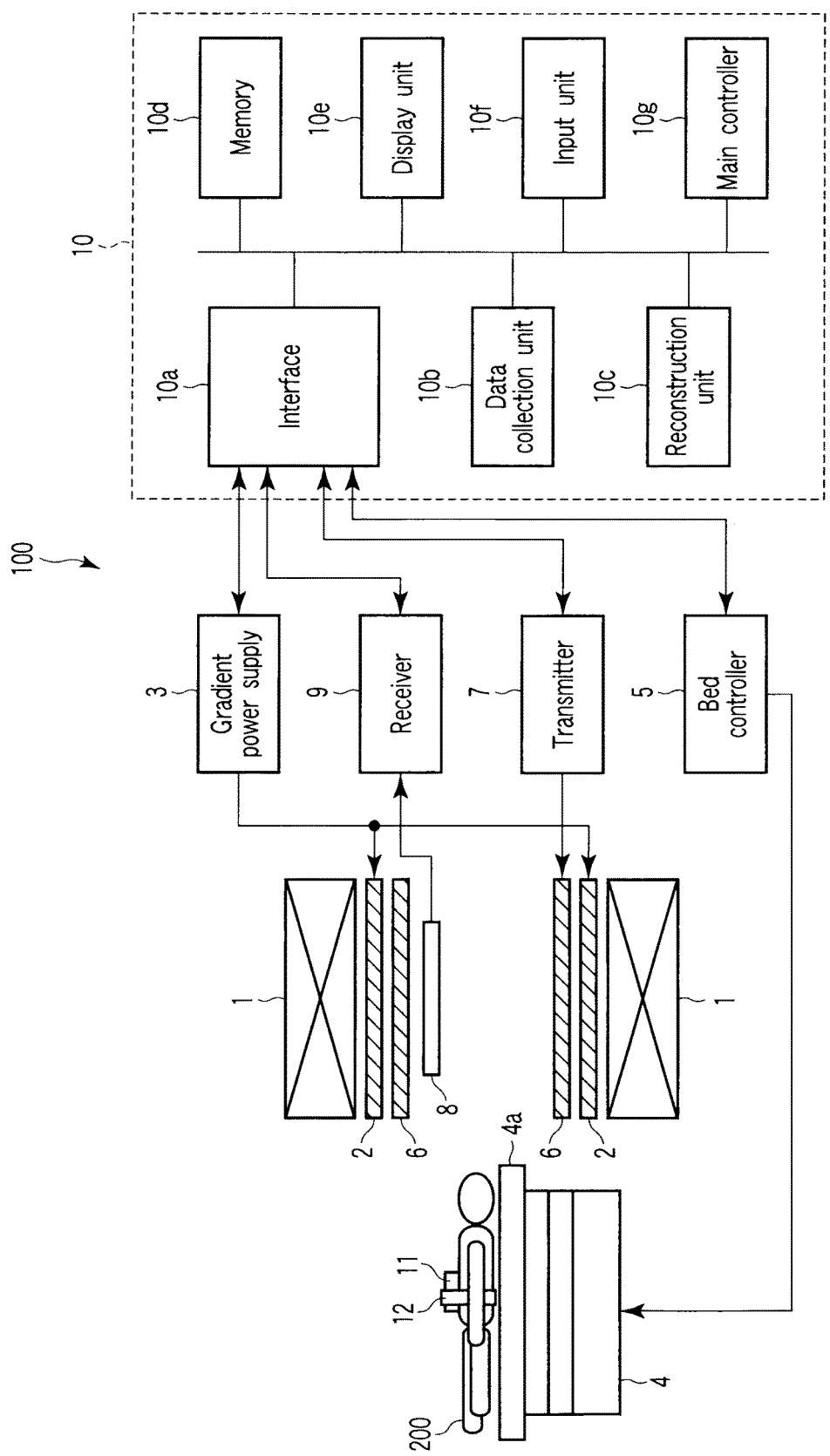
FIG. 1 shows the configuration of a magnetic resonance imaging apparatus according to a first embodiment.

FIG. 1 shows the configuration of a magnetic resonance imaging (MRI) apparatus, generally indicated at 100, according to a first embodiment. The MRI apparatus 100 includes a static field magnet 1, a gradient coil 2, a gradient power supply 3, a bed 4, a bed controller 5, a transmission RF coil 6, a transmitter 7, a receiving RF coil 8, a receiver 9, a computer system 10, and a respiration suppressing member 11.

The static field magnet 1 is formed in the shape of a hollow cylinder and adapted to generate a uniform static magnetic field within its inside shape. As the static field magnet 1 use is made of a permanent magnet, a superconducting magnet, or the like.

The gradient coil 2 is formed in the shape of a hollow cylinder and placed inside the static field magnet 1. The gradient coil 2 is a combination of three coils each corresponding to a respective one of the three mutually orthogonal X, Y and Z axes. When the three coils are individually supplied with current from the gradient power supply 3, the gradient coil 2 generates gradient magnetic fields each of which has its strength varied along a corresponding one of the X, Y and Z axes. Suppose that the Z-axis direction coincides with the direction of the static magnetic field. The gradient magnetic fields in the X, Y and Z-axis directions are used as a slice selecting gradient field Gs, a phase encoding gradient magnetic field Ge, and a readout gradient magnetic field Gr, respectively. The slice selecting gradient magnetic field Gs is used to arbitrarily determine an imaging plane section. The phase encoding gradient magnetic field Ge is used to change the phase of nuclear magnetic resonance (NMR) signals according to spatial location. The readout gradient magnetic field Gr is used to change the frequency of the NMR signals according to spatial location.

A subject 200 under examination is laid down on a top board 4a of the bed 4 and moved into the space of the gradient coil 2. The top board 4a is driven by the bed controller 5 to move in its lengthwise direction and in an up-and-down direction. Usually, the bed 4 is installed so that its lengthwise direction is parallel to the central axis of the static field magnet 1.

The transmitting RF coil 6 is placed inside the gradient coil 2 and generates a radio-frequency magnetic field in response to application thereto of a radio-frequency pulse from the transmitter 7.

The transmitter 7 has an oscillator, a phase selector, a frequency converter, an amplitude modulator, a radio-frequency power amplifier, etc., built in and transmits radio-frequency pulses corresponding to Larmor frequency to the transmitting RF coil 6.

The receiving RF coil 8 is placed inside the gradient coil 2 and adapted to receive NMR signals emitted from the human body under examination subjected to the radio-frequency magnetic field. The output signal from the receiving RF coil 8 is applied to the receiver 9.

The receiver 9 produces NMR signal data on the basis of the output signal of the receiving RF coil 8.

The computer system 10 includes an interface unit 10a, a data collection unit 10b, a reconstruction unit 10c, a memory unit 10d, a display unit 10e, an input unit 10f, and a main controller 10g.

The interface unit 10a is connected to the gradient power supply 3, the bed controller 5, the transmitter 7, the receiving RF coil 8, and the receiver 9 and allows signals to be transferred between each of these components and the computer system 10.

The data collection unit 10b collects via the interface unit 101 digital signals output from the receiver 9 and then stores the collected digital signals, i.e., the NMR signal data, into the memory unit 10d.

The reconstruction unit 10c performs postprocessing, i.e., reconstruction, such as Fourier transforms, on NMR signals data stored in the storage unit 10d to obtain spectrum data of desired nuclear spins within the subject 200 or image data.

The memory unit 10d stores NMR signal data and spectrum data or image data for each subject.

The display unit 10e displays a variety of information, such as spectrum data, image data, etc., under the control of the main controller 10g. As the display unit 10e there is available a display device, such as a liquid crystal display.

The input unit 10f receives a variety of commands and information inputs from an operator. As the input unit 10f there is available a pointing device, such as a mouse or trackball, a selection device, such as a mode changeover switch, or an input device, such as a keyboard.

The main controller 10g is equipped with a CPU, a memory, etc., which are not shown in the diagram and controls each component of the MRI apparatus 100.

The respiration suppressing member 11 is fixed to the abdomen of the subject 200 by a fixing belt 12.

FIG. 2A is a plan view of the respiration suppressing member 11. FIG. 2B is a side view of the respiration suppressing member 11. FIG. 2C is a sectional view taken along line A-A of FIG. 2B. FIG. 2D is a sectional view taken along line B-B of FIG. 2A.

As shown in FIGS. 2A, 2B, 2C and 2D, the respiration suppressing member 11 includes a rigid member 11a, an elastic member 11b, and a cover 11c.

The rigid member 11a is made from a highly rigid material, such as acryl, wood, etc., which is not easy to deform and formed in the shape of a triangular prism.

The rigid member 11a is covered with the elastic member 11b. The elastic member 11b is formed almost in the shape of a triangular prism by a moderately elastic material, such as urethane sponge. The nearly triangular plane formed by the elastic member 11b is much larger than that of the rigid member 11a. The rigid member 11a is placed in the proximity of one corner of the triangular plane formed by the elastic member 11b.

The cover 11c covers the elastic member 11b.

Of the respiration suppressing member 11, the triangular prism-shaped portion comprised of the rigid member 11a and its surrounding portions forms a pressurizing portion 11d which is higher in rigidity than the other portions of the mat. That is, the respiration suppressing member 11 forms an almost triangular prism which is larger than the pressurizing portion 11d. However, the respiration suppressing member 11 is only required to contain at least the pressurizing portion 11d. That is, other portions than the pressurizing portion 11d may be omitted. Furthermore, the shape of the other portions than the pressurizing portion 11d can be changed arbitrarily.

Figure 3:
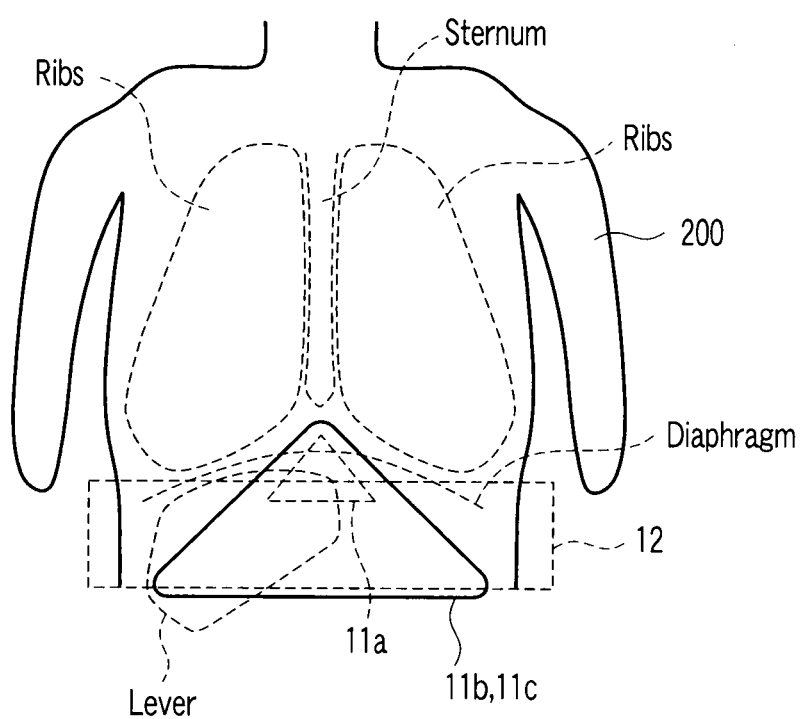
FIG. 3 is a diagram showing the state in which the respiration suppressing member shown in FIG. 1 is attached to the abdomen of a subject.

FIG. 3 shows the state in which the respiration suppressing member 11 is attached to the abdomen of the subject 200.

As shown in FIG. 3, the respiration suppressing member 11 is placed on the abdomen of the subject 200 with its triangular face in contact with the subject 200. The respiration suppressing member 11 is then fixed to the subject 200 by the fixing belt 12. At this point, it is desired that the respiration suppressing member 11 be placed such that the pressurizing portion 11d comes into contact with the abdomen of the subject 200 in the location below the sternum and between the left and right ribs, i.e., in the proximity of the pit of the stomach. Note here that "below the sternum" represents the direction of the subject's feet.

The respiration suppressing member 11 thus placed can effectively apply pressure to the pit of the stomach without coming into contact with the ribs. That is, the diaphragm can be pressurized by the pressurizing portion 11d without pressurizing the thorax. The respiration suppressing member 11 can sufficiently pressurize the diaphragm even without fastening the fixing belt 12 too tight because its any portion can touch the subject 200 well owing to moderate elasticity of the elastic member 11b. Moreover, the pressurizing portion 11d, having the rigid member 11a built in, is capable of sufficiently pressurizing the abdomen of the subject 200, while the other portions lightly pressurize the subject's abdomen owing to moderate elasticity of the elastic member 11b. Therefore, the respiration suppressing member 11 will not apply more pressure to the subject's abdomen that is necessary.

Thus, the respiration suppressing member 11 can effectively pressurize the diaphragm without imposing a heavy burden on the subject, so that the motion of the diaphragm pressurized by the respiration suppressing member 11 is suppressed.

WH MRCA imaging is carried out on the subject 200 with the respiration suppressing member 11 attached. That is, imaging scan is carried out on a desired region of the subject while monitoring the respiration-based motion of the subject under his or her natural respiration and changing the imaging position to fit the respiration-based motion, thereby collecting NMR signals. The respiration-based motion of the subject can be monitored by, for example, detecting the position of the diaphragm on the basis of the NMR signals. Based on the NMR signals thus collected, images associated with the desired region of the subject are reconstructed.

By so doing, it becomes possible to augment the possibility that the location of the diaphragm remains within an allowable range during the imaging scan, thus raising the rate of success in collection of NMR signals for imaging the coronary artery. As a result, the MRI apparatus 100 becomes enabled to image the coronary artery in a short period of time and with stability, good reproducibility and high accuracy.

Second Embodiment

The MRI apparatus according to a second embodiment is identical in configuration to the MRI apparatus 100 shown in FIG. 1. The MRI apparatus of the second embodiment is different from the MRI apparatus 100 in that a respiration suppressing member 13 is used in place of the respiration suppressing member 11.

FIG. 4A is a plan view of the respiration suppressing member 13. FIG. 4B is a side view of the respiration suppressing member 13. In FIGS. 3A and 3B, like reference numerals are used to denote corresponding parts to those in FIGS. 2A through 2D to thereby simplify the description.

As shown in FIGS. 4A and 4B, the respiration suppressing member 13 includes a rigid portion 11a, an elastic portion 11b, a cover 11c, a pressure sensor 13a, and a vibrator 13b. Though not shown in FIGS. 4A and 4B, the respiration suppressing member 13 further includes a drive circuit 13c as shown in FIG. 5. That is, the respiration suppressing member 13 is constructed such that the pressure sensor 13a, the vibrator 13b and the drive circuit 13c are added to the base structure of the respiration suppressing member 11 of the first embodiment.

The pressure sensor 13a and the vibrator 13b are attached to the rigid member 11a. The pressure sensor 13a detects pressure applied by the abdomen of the subject 200 to the respiration suppressing member 13 to output a detected signal. As the pressure sensor 13a use may be made of, for example, a piezoelectric element. The vibrator 13b vibrates in response to a drive signal from the drive circuit 13c. As the vibrator 13b use may be made of, for example, a piezoelectric element by way of example. The drive circuit 13c responds to the detected signal from the pressure sensor 13a to apply a drive signal to the vibrator 13b. The drive circuit 13c, while it is typically attached to the rigid member 11a, may be placed inside the elastic member 11b apart from the rigid member 11a. It is desirable to place the drive circuit 13c apart from the rigid member 11a or shield it in order to minimize the effect of its noise.

The respiration suppressing member 13 is attached to the abdomen of the subject 200 as shown in FIG. 6B in the same manner as the respiration suppressing member 11. However, that face of the suppressing member 13 which is nearer to the pressure sensor 13a and the vibrator 13b is directed to the subject 200.

In the respiration suppressing member 13 thus attached to the abdomen of the subject 200, the pressure applied to it by the abdomen varies according to the respiration-based motion of the abdomen. The pressure sensor 13a detects the pressure thus varying to output a corresponding detected signal. The drive circuit 13c monitors the detected signal and, when the detected signal exceeds a specified level, outputs a drive signal to the vibrator 13b to vibrate it. The vibration of the vibrator 13b is transmitted to the subject 200 via the elastic member 11b and the cover 11c.

Thus, when the respiration level of the subject reaches a fixed depth, the respiration suppressing member 13 vibrates. Therefore, based on the vibration of the respiration suppressing member 13, the subject is allowed to recognize that his or her own respiration level has reached a specified depth. If the subject adjusts his or her own respiration so that the respiration level can be maintained at the fixed depth, it becomes possible to further improve the probability that the location of the diaphragm remains in the allowable range during imaging by WH MRCA.

By providing the respiration suppressing member 13 with operating means and causing the operating means to supply the drive circuit 13c with a setting signal corresponding to an operation of a user or supplying an externally applied setting signal to the drive circuit 13c to thereby allow the drive circuit to change the specified level, the abovementioned operation can be performed using an appropriate specified level which allows for the difference in respiration level among subjects. In this case, it is desirable to statistically determine a feature value, such as a most frequent value of the respiration level when a subject is caused to naturally respire several times, and set a specified level with reference to that value. Further, it is also possible to automatically set such a specified level by presetting the number of times of natural respiration.

Third Embodiment

The MRI apparatus according to a third embodiment is identical in configuration to the MRI apparatus 100 shown in FIG. 1. The MRI apparatus of the third embodiment is different from the MRI apparatus 100 in that a respiration suppressing member 14 is used in place of the respiration suppressing member 11.

Figure 7A:
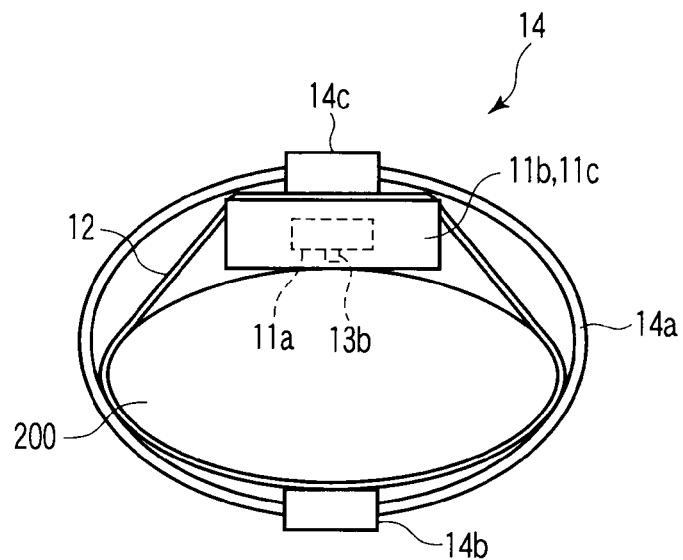
FIG. 7A is an exterior view of a respiration suppressing member of a third embodiment as viewed along the direction of the body axis of a subject.
Figure 7B:
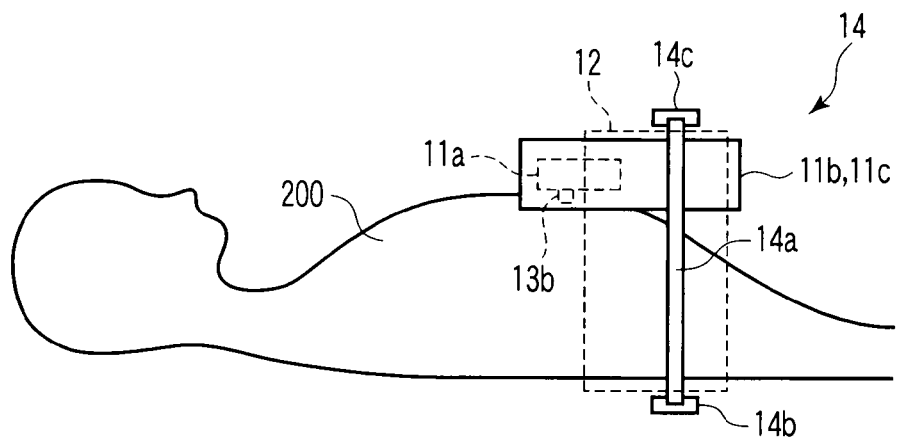
FIG. 7B is an exterior view of the respiration suppressing member of the third embodiment as viewed from the side of the subject.

FIG. 7A shows the respiration suppressing member 14 as viewed in the direction of the body axis of the subject 200. FIG. 7B shows the respiration suppressing member 14 as viewed from the side of the subject 200. In FIGS. 7A and 7B, like reference numerals are used to denote corresponding parts to those in FIGS. 2A through 2D or FIGS. 4A and 4B to thereby simplify the description.

Figure 8:
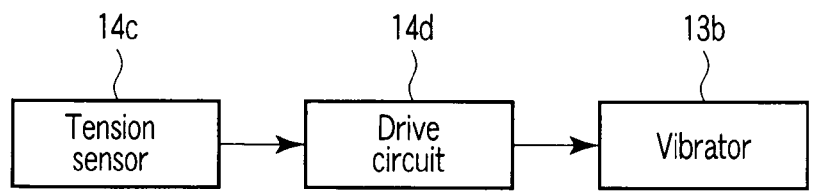
FIG. 8 shows an electrical arrangement of the respiration suppressing member of the third embodiment.

As shown in FIGS. 7A and 7B, the respiration suppressing member 14 includes a rigid portion 11a, an elastic portion 11b, a cover 11c, a vibrator 13b, a bellows 14a, a tension generator 14b, and a tension sensor 14c. Though not shown in FIGS. 7A and 7B, the respiration suppressing member 14 further includes a drive circuit 14d as shown in FIG. 8. That is, the respiration suppressing member 14 is constructed such that the vibrator 13b, the bellows 14a, the tension generator 14b, the tension sensor 14c and the drive circuit 14d are added to the base structure of the respiration suppressing member 11 of the first embodiment.

The bellows 14a is arranged in the form of a ring on the peripheral side of the fixing belt 12. The tension generator 14b gives tension to the bellows 14a as required. The tension sensor 14c outputs a detected signal corresponding to tension applied to the bellows 14a. The drive circuit 14d monitors the detected signal and supplies the drive circuit 13b with a drive signal when the detected signal reaches a specified level. The drive circuit 14d drives the tension generator 14b when there is need to apply tension to the bellows 14a.

The respiration suppressing member 14 has its portion constructed from the rigid member 11a, the elastic member 11b and the cover 11c (hereinafter referred to as the main body) attached to the abdomen of the subject 200 in the same manner as the respiration suppressing member 11 of the first embodiment as shown in FIG. 7A. At this point, that face of the respiration suppressing member 14 which is nearer to the vibrator 13b is directed to the subject 200 as shown in FIG. 7B. Further, the bellows 14a, the tension generator 14b and the tension sensor 14c are arranged on the peripheral side of the fixing belt 12 as shown in FIGS. 7A and 7B. The bellows 14 may be omitted, in which case the tension generator 14b and the tension sensor 14c are attached to the fixing belt 12.

In operation, the respiration suppressing member 14 has its main body moved by respiration-based motion of the abdomen of the subject 200 and as a result the tension applied to the bellows 14a varies. The tension sensor 14c detects the tension thus varying and outputs a detected signal corresponding to the detected tension. The drive circuit 14d monitors the detected signal and applies a drive signal to the vibrator 13b when the detected signal reaches a specified level to drive the vibrator. The vibration of the vibrator 13b is transmitted to the subject 200 through the elastic member 11b and the cover 11c.

Thus, the third embodiment can also provide the same advantages as the second embodiment.

Fourth Embodiment

The MRI apparatus according to a fourth embodiment is identical in configuration to the MRI apparatus 100 of the first embodiment shown in FIG. 1. The MRI apparatus of the fourth embodiment is different from the MRI apparatus 100 in that a respiration suppressing member 15 is used in place of the respiration suppressing member 11.

Figure 9A:
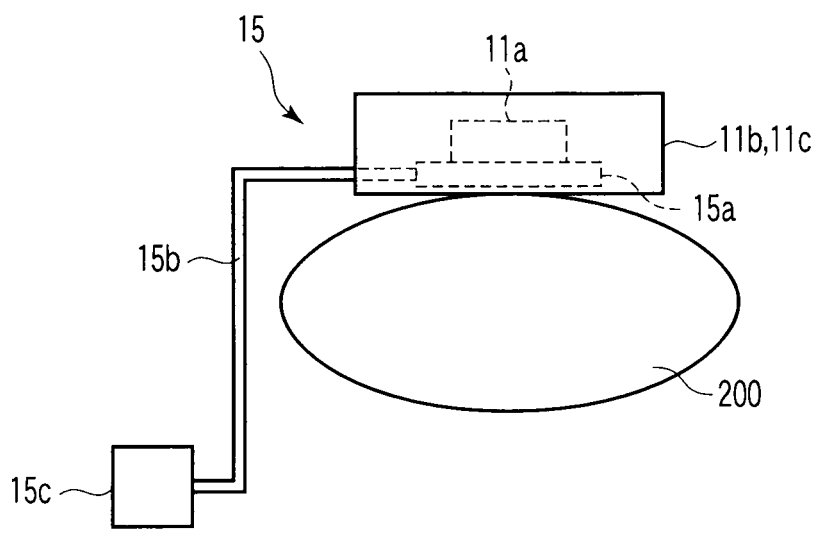
FIG. 9A is an exterior view of a respiration suppressing member of a fourth embodiment as viewed along the direction of the body axis of a subject.
Figure 9B:
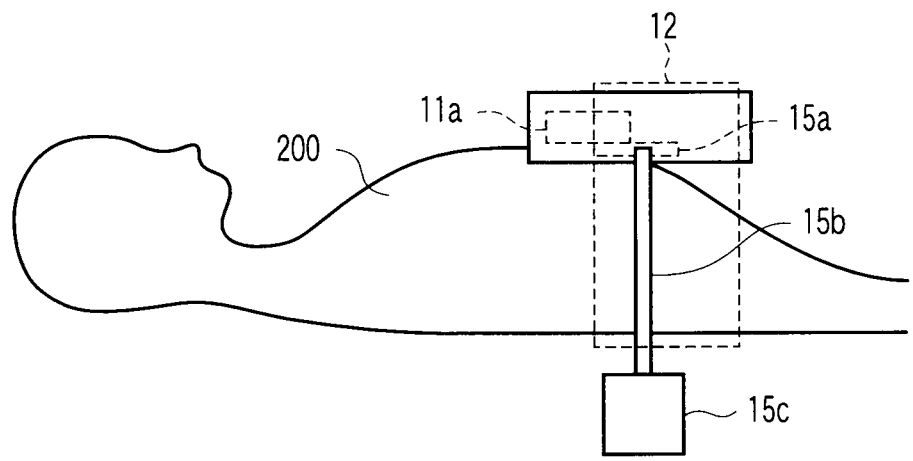
FIG. 9B is an exterior view of the respiration suppressing member of the fourth embodiment as viewed from the side of the subject.

FIG. 9A shows the respiration suppressing member 15 as viewed in the direction of the body axis of the subject 200. FIG. 9B shows the respiration suppressing member 15 as viewed from the side of the subject 200. In FIGS. 9A and 9B, like reference numerals are used to denote corresponding parts to those in FIGS. 2A through 2D to thereby simplify the description.

Figure 10:
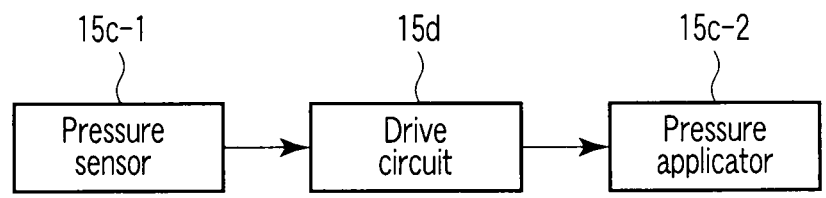
FIG. 10 shows an electrical arrangement of the respiration suppressing member of the fourth embodiment.

As shown in FIGS. 9A and 9B, the respiration suppressing member 15 includes a rigid portion 11a, an elastic portion 11b, a cover 11c, a puff 15a, a rigid pipe 15b, and a pressure sensor/applicator 15c. Though not shown in FIGS. 9A and 9B, the respiration suppressing member 15 further includes a drive circuit 15d as shown in FIG. 10. That is, the respiration suppressing member 15 is constructed such that the puff 15a, the rigid pipe 15b, the pressure sensor/applicator 15c and the drive circuit 14d are added to the base structure of the respiration suppressing member 11 of the first embodiment.

The puff 15a consists of a hollow resin which is so soft as to be easy to deform and contains a medium, such as air or liquid, in it. The rigid pipe 15b is linked to the puff 15a and contains the above medium. The pressure sensor/applicator 15c is equipped with a pressure sensor 15c-1 and a pressure applicator 15c-2. The pressure sensor 15c is linked to the rigid pipe 15b and outputs a detected signal corresponding to pressure of the medium in the rigid pipe. The pressure applicator 15c is linked to the rigid pipe 15b to apply pressure to the medium in the rigid pipe. The drive circuit 15d monitors the detected signal and, when the detected signal reaches a specified level, drives the pressure applicator 15c-2 so as to apply pressure to the medium.

The respiration suppressing member 15 has its portion constructed from the rigid member 11a, the elastic member 11b and the cover 11c (hereinafter referred to as the main body) attached to the abdomen of the subject 200 in the same manner as the respiration suppressing member 11 of the first embodiment as shown in FIG. 9A. At this point, that face of the respiration suppressing member 15 which is nearer to the puff 15a is directed to the subject 200 as shown in FIG. 9B.

In operation, in the respiration suppressing member 15, pressure applied to the puff 15a is varied by respiration-based motion of the abdomen of the subject 200. As a result, the pressure of the medium contained in the puff 15a and the rigid pipe 15b also varies. The pressure sensor 15c-1 detects the thus varying pressure and outputs a detected signal corresponding to the detected pressure. The drive circuit 15d monitors the detected signal and applies a drive signal to the pressurizeer 15c-2 when the detected signal reaches a specified level. Upon receipt of the drive signal, the pressure applicator 15c-2 applies pressure to the medium to expand the puff 15a. The expansion of the puff 15a varies the pressure applied by the main body to the subject 200.

The respiration suppressing member 15 may be equipped with two rigid pipes, in which case each rigid pipe is individually fitted with a pressure sensor 15c-1 and a pressure applicator 15c-2.

Thus, variations in the pressure applied to the subject allows the subject to recognize that his or her own respiration level has reached a specified depth as in the second embodiment.

Fifth Embodiment

Figure 11:
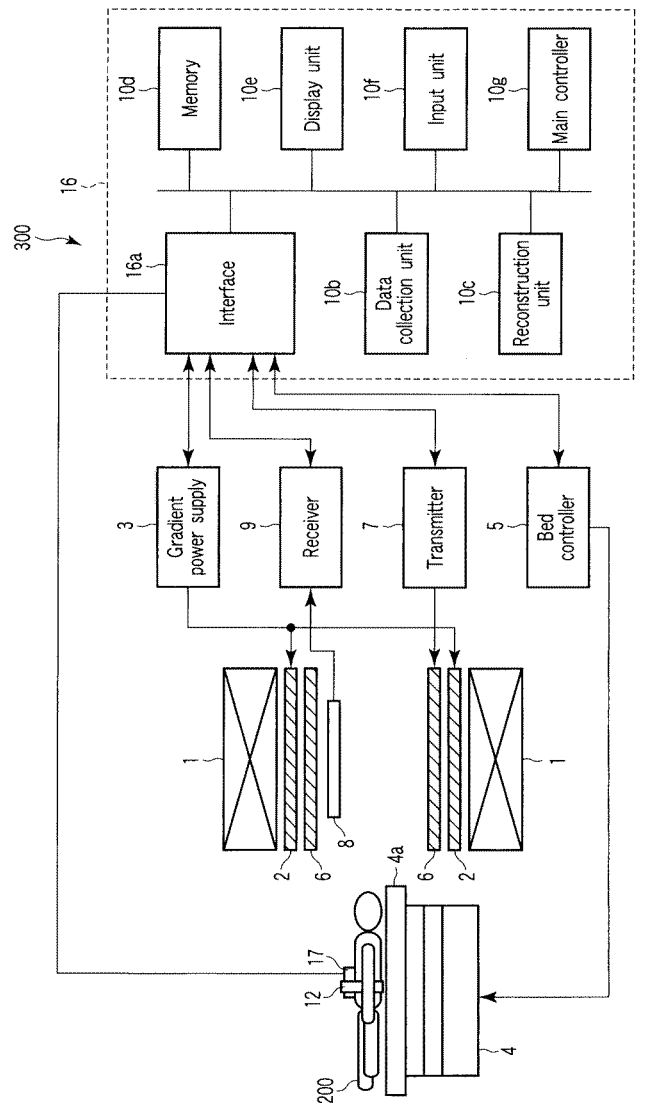
FIG. 11 shows the configuration of a magnetic resonance imaging apparatus according to a fifth embodiment.
Figure 12A:
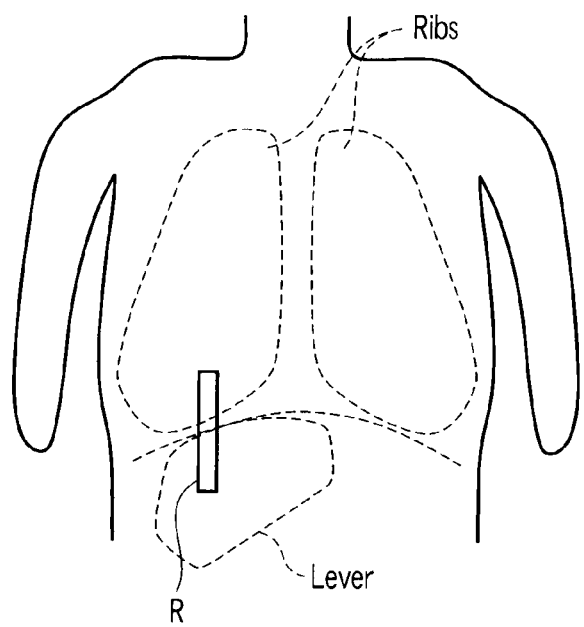
FIGS. 12A, 12B and 12C are diagrams for use in explanation of a prior art.
Figure 12B:
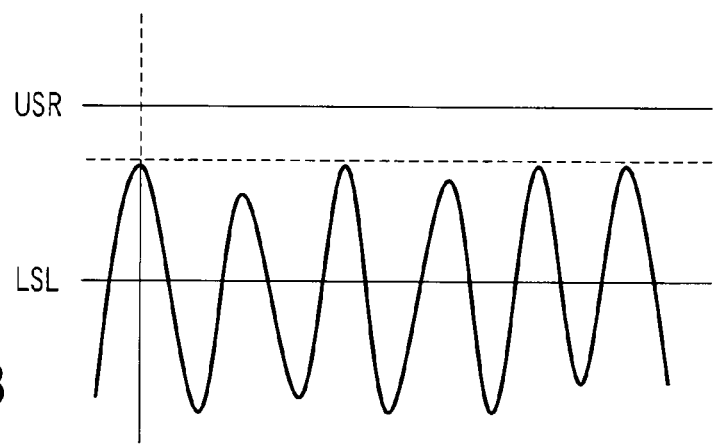
Figure 12C:
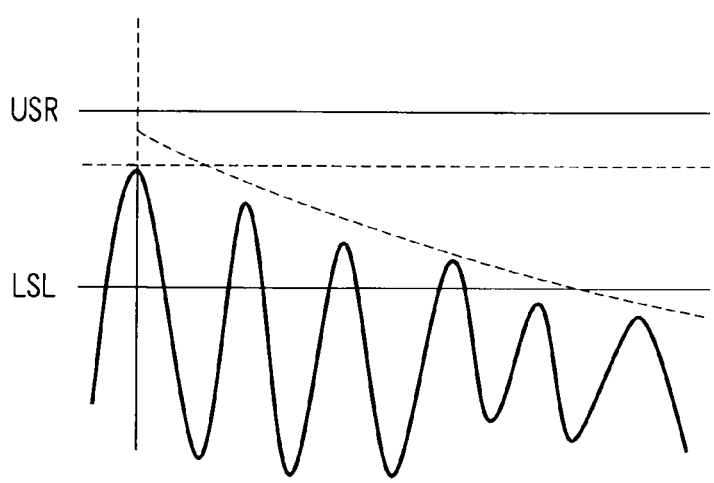
Figure 13:
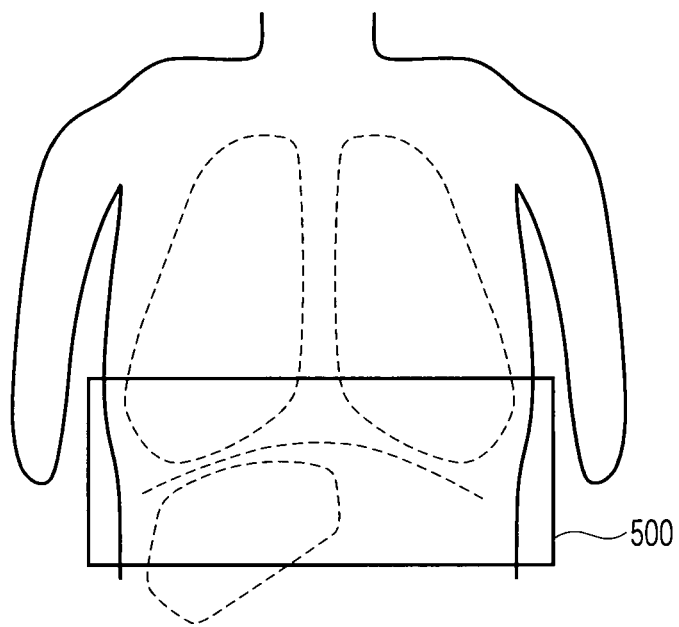
FIG. 13 is a diagram for use in explanation of a prior art.

FIG. 11 shows the configuration of an MRI apparatus 300 according to a fifth embodiment. In FIG. 11, like reference numerals are used to denote corresponding parts to those in FIG. 1 to thereby simplify the description.

This MRI apparatus 300 includes a static field magnetic 1, a gradient coil 2, a gradient power supply 3, a bed 4, a bed controller 5, a transmission RF coil 6, a transmitter 7, a receiving RF coil 8, a receiver 9, a computer system 16, and a respiration suppressing member 17. That is, the MRI apparatus 300 is equipped with the computer system 16 and the respiration suppressing member 17 in place of the computer system 10 and the respiration suppressing member 13 in the MRI apparatus 100.

The computer system 16 includes a data collection unit 10b, a reconstruction unit 10c, a memory unit 10d, a display unit 10e, an input unit 10f, an interface unit 16a, and a main controller 16b. That is, the computer system 16 is equipped with the interface unit 16a and the main controller 16b in place of the interface unit 10a and the main controller 10g in the computer system 10.

The interface unit 16a is connected to the respiration suppressing member 17 as well as the gradient power supply 3, the bed controller 5, the transmitter 7, the receiving RF coil 8, and the receiver 9. The interface unit allows signals to be transferred between each of these components and the computer system 16.

The main controller 16b is equipped with a CPU, a memory, etc., which are not shown in the diagram and controls each component of the MRI apparatus 300. The main controller 16b has a function of monitoring the respiration level of the subject 200 on the basis of NMR signals from the diaphragm and applying a drive signal to the respiration suppressing member 17 when the respiration level reaches a specified level.

The respiration suppressing member 17 is fixed to the abdomen of the subject 200 by a fixing belt 12. The respiration suppressing member 17 is constructed such that a notification unit is added to the base structure of the respiration suppressing member 11 of the first embodiment. As the notification unit use may be made of the vibrator 13b in the second embodiment or the puff 15a, the rigid pipe 15b and the pressure applicator 15c-2 in the fourth embodiment. The notification unit responds to the drive signal from the main controller 16b to provide a notification operation based on vibration or pressurizing.

At the time of imaging the coronary artery by the MRI apparatus 300, the main controller 16b monitors the respiration level of the subject 200 using NMR signals from the diaphragm and applies a drive signal to the respiration suppressing member 17 when the respiration level is at a specified level. In the respiration suppressing member 17, the notification unit responds to that drive signal to perform a notification operation.

Thus, the fifth embodiment can also provide the same advantages as the second embodiment. Furthermore, the fifth embodiment can detect the respiration level of the subject 200 with higher accuracy than the second, third and fourth embodiments, thus allowing the subject 200 to receive notification at a more appropriate time.

The embodiments can be variously modified as follows:

The pressure applicator may be formed in the shape of a circular cylinder or a polygonal prism having more than four angles provided that it can apply pressure to the diaphragm without pressurizing the ribs excessively. Alternatively, it may be formed in any other shape.

The rigid portion 11a can be omitted by causing the elastic member 11b to have rigidity sufficient to pressurize the diaphragm. In this case, the elastic member 11b should be formed into such a shape as will not pressurize the ribs excessively like a triangular prism. That is, it is also possible to realize the pressure applicator as a part of the elastic member 11b.

The subject may receive notification when the respiration level is in a specified range, i.e., between upper- and lower-limiting thresholds.

The notification mode can be changed by setting a number of specified levels or ranges and changing the vibration pattern depending on which specified level or range the respiration level of the subject matches.

The notification to the subject may be made based on the relationship between a reference pressure value and a pressure level detected by a pressure sensor attached to the abdomen of the subject. In this case, however, there is an error between a respiration level based on an NMR signal and that based on the pressure level detected by the pressure sensor. Further, since a certain time is required to detect a respiration level from an NMR signal, the respiration level based on the NMR signal is acquired slightly later than that based on the pressure level detected by the pressure sensor. In light of this, before starting data collection for imaging, the respiration level of the subject is simultaneously monitored using the NMR signal and the pressure level detected by the pressure sensor, thereby detecting an error in respiration level therebetween and a delay therebetween in detecting the respiration level. It is desirable, in consideration of the detected error and delay, to set an appropriate reference pressure value or to correct a respiration level obtained from the pressure level detected by the pressure sensor.

The respiration level can be detected using some other sensor, such as a height sensor. Further, the notification to the subject may be made based on a respiration level detected by a known respiration synchronization unit.

The vibrator 13b or the puff 15a may be formed into a sheet-like member which is inserted between the cover 11c and the subject 200 or a member that the subject holds.

The notification may be made through sound, light, or tension. Further, sound, light or tension may be used in combination with vibration, air pressure or liquid pressure. For example, in the case of light, notification can be made through projection of light into the gantry, projection of light to walls, transmission of light through small-sized glasses, LEDs arranged up and down, or a indicator. It is also possible to let the subject to see light from such a light source through an optical fiber.

The main controller 10g or 16b may control the application of a drive signal to the notification unit on the basis of a detected signal from the pressure sensor 13a or pressure sensor 15c-1 or the tension sensor 14c, in which case the detected signal is sent to the computer system 10 or 16.

The signal transmission within the respiration suppressing member 11, 13, 14 or 15 or between the respiration suppressing member 11, 13, 14 or 15 and the computer system 10 may be made by using a normal signal line or optical fiber, or by radio.

The medical modality may be not only an MRI apparatus but also an X-ray diagnostic apparatus, a computed tomography (CT) apparatus, a positron emission computed tomography (PET) apparatus, or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging system comprising:
   a respiration suppressor, the respiration suppressor including a notifier that responds to a drive signal to perform a notification operation perceptible by a subject, wherein the respiration suppressor is configured to be placed on the abdomen of the subject, and further configured to apply pressure to the abdomen, wherein the abdomen is located below the sternum and between the right and left ribs of the subject; and
   a magnetic resonance imaging apparatus comprising:
     a static field magnet which generates a static magnetic field;
     circuitry configured to apply a radio-frequency magnetic field and gradient magnetic fields to the subject placed in the static magnetic field in accordance with a pulse sequence; and
     a receiver which receives magnetic resonance signals, which are emitted from the subject by being subjected to the radio-frequency magnetic field and the gradient magnetic fields, of the subject in a state in which pressure is applied to the abdomen but not to the thorax of the subject by the respiration suppressor,
   wherein the circuitry is further configured to;
   obtain a respiration-based motion signal representative of respiration-based motion of the subject by determining a location of the diaphragm of the subject on the basis of the magnetic resonance signals received by the receiver;
   control a supply of the radio-frequency magnetic field and the gradient magnetic fields to receive the magnetic resonance signals, by means of an imaging scan of the heart of the subject while changing an imaging position in synchronism with the respiration-based motion signal, by the receiver;
   reconstruct an image associated with the heart on the basis of the magnetic resonance signals received by the receiver; and
   apply the drive signal to the notifier on the basis of the determination of the location of the diaphragm.

2. The magnetic resonance imaging system according to claim 1, wherein the respiration suppressor comprises a main body comprising an elastic material and a pressurizing portion configured to apply pressure to the abdomen.

3. The magnetic resonance imaging system according to claim 2, wherein the pressurizing portion has a shape of a triangular prism.

4. The magnetic resonance imaging system according to claim 3, wherein the main body has the shape of the triangular prism which contains the pressurizing portion and is larger than the pressurizing portion.

5. The magnetic resonance imaging system according to claim 2, wherein the pressurizing portion contains a core material which is more rigid than the elastic material.

6. The magnetic resonance imaging system according to claim 1, wherein the notifier includes a vibrator which responds to the drive signal to vibrate.

7. The magnetic resonance imaging system according to claim 6, wherein the vibrator is equipped with a piezoelectric element.

8. The magnetic resonance imaging system according to claim 2, wherein the pressurizing portion has one of a cylindrical shape and a polygonal prism shape.

9. The magnetic resonance imaging system according to claim 1, wherein the notification operation by the notifier is visible by the subject.

10. A non-transitory computer-readable medium storing computer readable instructions thereon that when executed by a computer cause the computer to perform a method comprising the steps of:
    receiving magnetic resonance signals, which are emitted from a subject by being subjected to a radio-frequency magnetic field and gradient magnetic fields;
    obtaining a signal representative of the a respiration-based motion of the subject in a state in which pressure is applied to a portion of the abdomen but not to the thorax of the subject, the abdomen being located below the sternum and between the right and left ribs of the subject, the pressure being applied by a respiration suppressor, the respiration suppressor including a notifier that responds to a drive signal to perform a notification operation perceptible by the subject;
    controlling a supply of the radio-frequency magnetic field and the gradient magnetic fields so as to collect magnetic resonance signals by means of an imaging scan of the heart of the subject while changing an imaging position in synchronism with the signal representative of the respiration-based motion of the subject in said state; and
    reconstructing an image of the heart of the subject on the basis of the collected magnetic resonance signals: and
    applying the drive signal to the respiration suppressor.

* * * * *